(12) United States Patent
Steffen et al.

(10) Patent No.: US 8,852,200 B2
(45) Date of Patent: Oct. 7, 2014

(54) DEVICE FOR INJECTING HIGH VISCOSITY MATERIAL

(75) Inventors: Thomas Steffen, Montreal (CA); Lorne Beckman, Montreal (CA); Demetrios Giannitsios, Montreal (CA)

(73) Assignees: Thomas Steffen, Montreal (CA); Lorne Beckman, Montreal (CA); Demetrios Giannitsios, Edmonton (CA)

( * ) Notice: Subject to any disclaimer, the term of this patent is extended or adjusted under 35 U.S.C. 154(b) by 1173 days.

(21) Appl. No.: 12/044,046

(22) Filed: Mar. 7, 2008

(65) Prior Publication Data

US 2008/0243129 A1 Oct. 2, 2008

Related U.S. Application Data

(63) Continuation of application No. PCT/CA2006/001487, filed on Sep. 7, 2006.

(60) Provisional application No. 60/714,343, filed on Sep. 7, 2005.

(51) Int. Cl.
| | |
|---|---|
| *A61B 17/58* | (2006.01) |
| *A61B 17/60* | (2006.01) |
| *A61F 2/00* | (2006.01) |
| *A61F 2/46* | (2006.01) |
| *A61F 2/44* | (2006.01) |
| *A61B 17/00* | (2006.01) |
| *A61M 5/44* | (2006.01) |
| *A61M 5/145* | (2006.01) |
| *A61B 17/88* | (2006.01) |

(52) U.S. Cl.
CPC ............ *A61N 5/1483* (2013.01); *A61F 2/4601* (2013.01); *A61F 2/44* (2013.01); *A61B 2017/00539* (2013.01); *A61M 5/445* (2013.01); *A61M 2005/14513* (2013.01); *A61B 17/8822* (2013.01)
USPC .............................................. 606/94; 606/93

(58) Field of Classification Search
CPC ............. A61B 17/545; A61B 17/7061; A61B 17/8822; A61B 17/8825
USPC ............... 606/93, 191, 201, 86 R, 92–94, 53; 604/6.1, 99.02, 99.03, 99.04, 167.03, 604/236
See application file for complete search history.

(56) References Cited

U.S. PATENT DOCUMENTS 2,653,605 A * 9/1953 Hein, Jr. ......................... 604/70
3,279,660 A 10/1966 Collar
(Continued)

FOREIGN PATENT DOCUMENTS

| FR | 2717085 | 9/1995 |
|---|---|---|
| WO | 9637150 | 11/1996 |
| WO | 2005/077443 | 8/2005 |

OTHER PUBLICATIONS

English translation of the abstract of Russian patent reference RU2317111 C1.
(Continued)

*Primary Examiner* — David Bates
*Assistant Examiner* — Samuel Hanna
(74) *Attorney, Agent, or Firm* — Norton Rose Fulbright Canada LLP

(57) ABSTRACT

A device for injecting a high viscosity material into a cannula, comprising a container being non-compliant and having an outlet adapted to communicate with the cannula for transferring the high viscosity material thereto, a pressure applicator in fluid communication with the container, the pressure applicator defining a fluid flow path through which an incompressible fluid is displaceable, and a material-moving member interrupting the fluid flow path and defining an incompressible fluid receiving portion on one side thereof in communication with the fluid flow path and a high viscosity material receiving portion in communication with the outlet of the container on an opposed side. The material-moving member being displaceable by a pressure of the incompressible fluid acting thereagainst to force the high viscosity material out of the high viscosity material receiving portion of the container and into the cannula.

12 Claims, 14 Drawing Sheets

(56) References Cited

U.S. PATENT DOCUMENTS

| | | | |
|---|---|---|---|
| 4,200,259 A * | 4/1980 | Ueda | 251/285 |
| 4,250,887 A | 2/1981 | Darkik et al. | |
| 4,323,067 A * | 4/1982 | Adams | 604/74 |
| 4,345,594 A * | 8/1982 | Bisera et al. | 604/69 |
| 5,254,092 A | 10/1993 | Polyak | |
| 5,411,180 A | 5/1995 | Dumelle | |
| 5,431,654 A | 7/1995 | Nic | |
| 5,514,135 A | 5/1996 | Earle | |
| 5,638,997 A | 6/1997 | Hawkins et al. | |
| 5,743,960 A * | 4/1998 | Tisone | 118/683 |
| 5,906,802 A | 5/1999 | Langford | |
| 6,126,682 A | 10/2000 | Sharkey | |
| 6,348,055 B1 | 2/2002 | Preissman | |
| 6,406,175 B1 | 6/2002 | Marino | |
| 6,425,897 B2 | 7/2002 | Overes et al. | |
| 6,547,432 B2 | 4/2003 | Coffeen et al. | |
| 6,582,446 B1 | 6/2003 | Marchosky | |
| 6,974,247 B2 | 12/2005 | Frei et al. | |
| 7,008,433 B2 | 3/2006 | Voellmicke et al. | |
| 7,112,205 B2 | 9/2006 | Carrison | |
| 7,371,241 B2 | 5/2008 | Evans et al. | |
| 7,393,342 B2 | 7/2008 | Henniges et al. | |
| 7,524,103 B2 | 4/2009 | McGill et al. | |
| 7,922,690 B2 | 4/2011 | Plishka et al. | |
| 8,070,728 B2 | 12/2011 | Baroud | |
| 8,235,256 B2 | 8/2012 | Green et al. | |
| 8,246,628 B2 | 8/2012 | Rabiner | |
| 8,257,310 B2 | 9/2012 | Donovan et al. | |
| 8,333,773 B2 | 12/2012 | Dimauro et al. | |
| 8,348,956 B2 | 1/2013 | Rabiner | |
| 8,409,211 B2 | 4/2013 | Baroud | |
| 2004/0030345 A1 | 2/2004 | Aurin et al. | |
| 2004/0193171 A1 | 9/2004 | DiMauro et al. | |
| 2004/0260303 A1 | 12/2004 | Carrison | |
| 2005/0070915 A1 * | 3/2005 | Mazzuca et al. | 606/93 |
| 2005/0113843 A1 | 5/2005 | Arramon | |
| 2005/0180806 A1 | 8/2005 | Green et al. | |
| 2006/0052794 A1 * | 3/2006 | McGill et al. | 606/93 |
| 2006/0133193 A1 | 6/2006 | Arramon | |
| 2006/0264964 A1 | 11/2006 | Scifert et al. | |
| 2006/0264967 A1 | 11/2006 | Ferreyro et al. | |
| 2007/0233146 A1 | 10/2007 | Henniges et al. | |
| 2007/0233149 A1 | 10/2007 | Bohner et al. | |
| 2007/0287958 A1 * | 12/2007 | McKenzie et al. | 604/131 |
| 2008/0039856 A1 | 2/2008 | DiMauro | |
| 2008/0195114 A1 | 8/2008 | Murphy | |
| 2008/0243129 A1 | 10/2008 | Steffen | |
| 2008/0255571 A1 | 10/2008 | Truckai et al. | |
| 2009/0264942 A1 | 10/2009 | Beyar | |
| 2009/0270872 A1 | 10/2009 | DiMauro | |
| 2010/0087828 A1 | 4/2010 | Krueger et al. | |
| 2010/0114174 A1 | 5/2010 | Jones et al. | |
| 2010/0274080 A1 | 10/2010 | Donovan et al. | |
| 2010/0274255 A1 | 10/2010 | Donovan et al. | |
| 2011/0015641 A1 | 1/2011 | Matsumoto | |
| 2011/0112543 A1 | 5/2011 | Palazzolo | |

OTHER PUBLICATIONS

English translation of the abstract of Russian patent reference RU72136.
Machine translation into English of FR2717085.
European Search Report issued in corresponding European Patent Application No. 11180263.3.

* cited by examiner

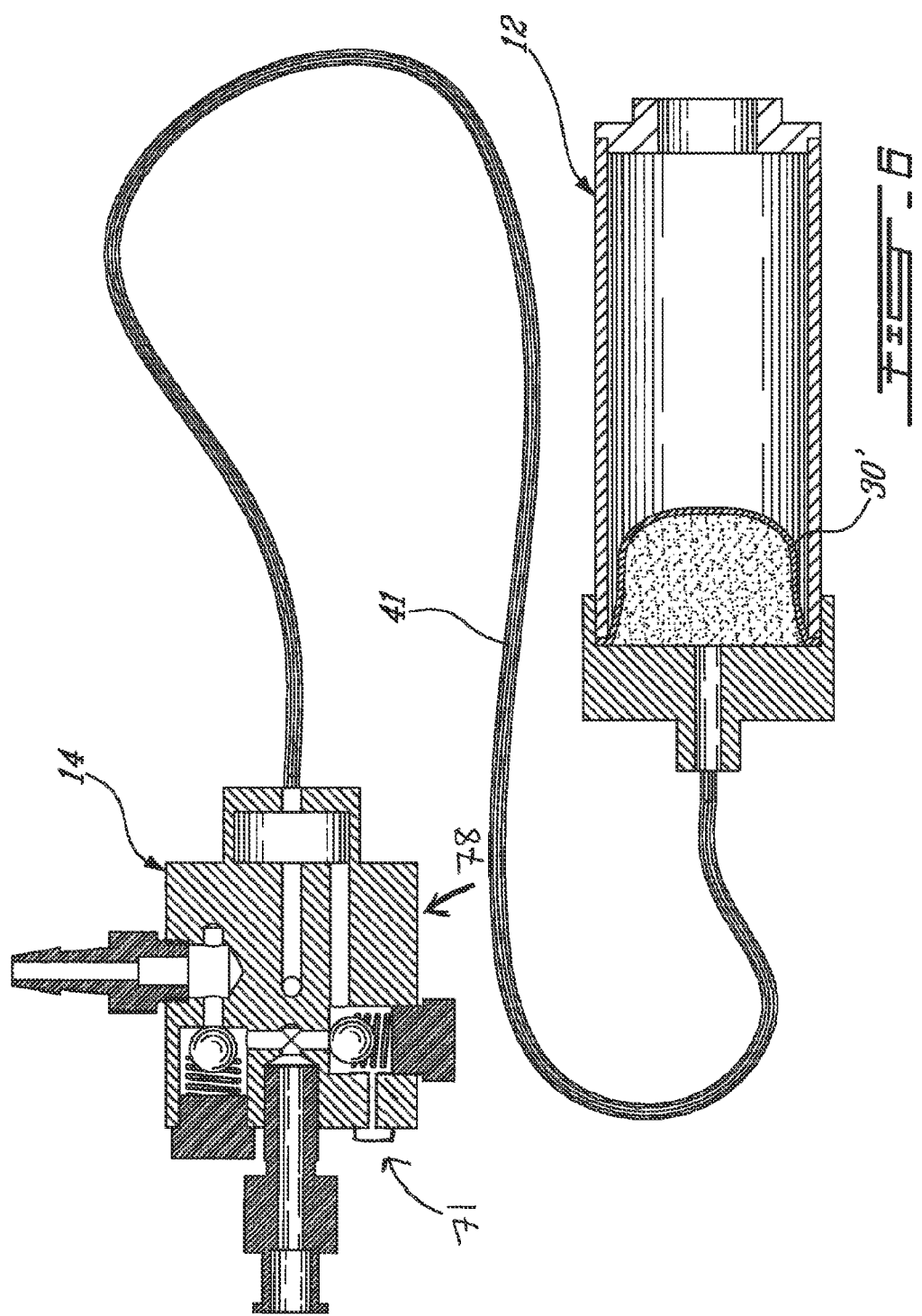

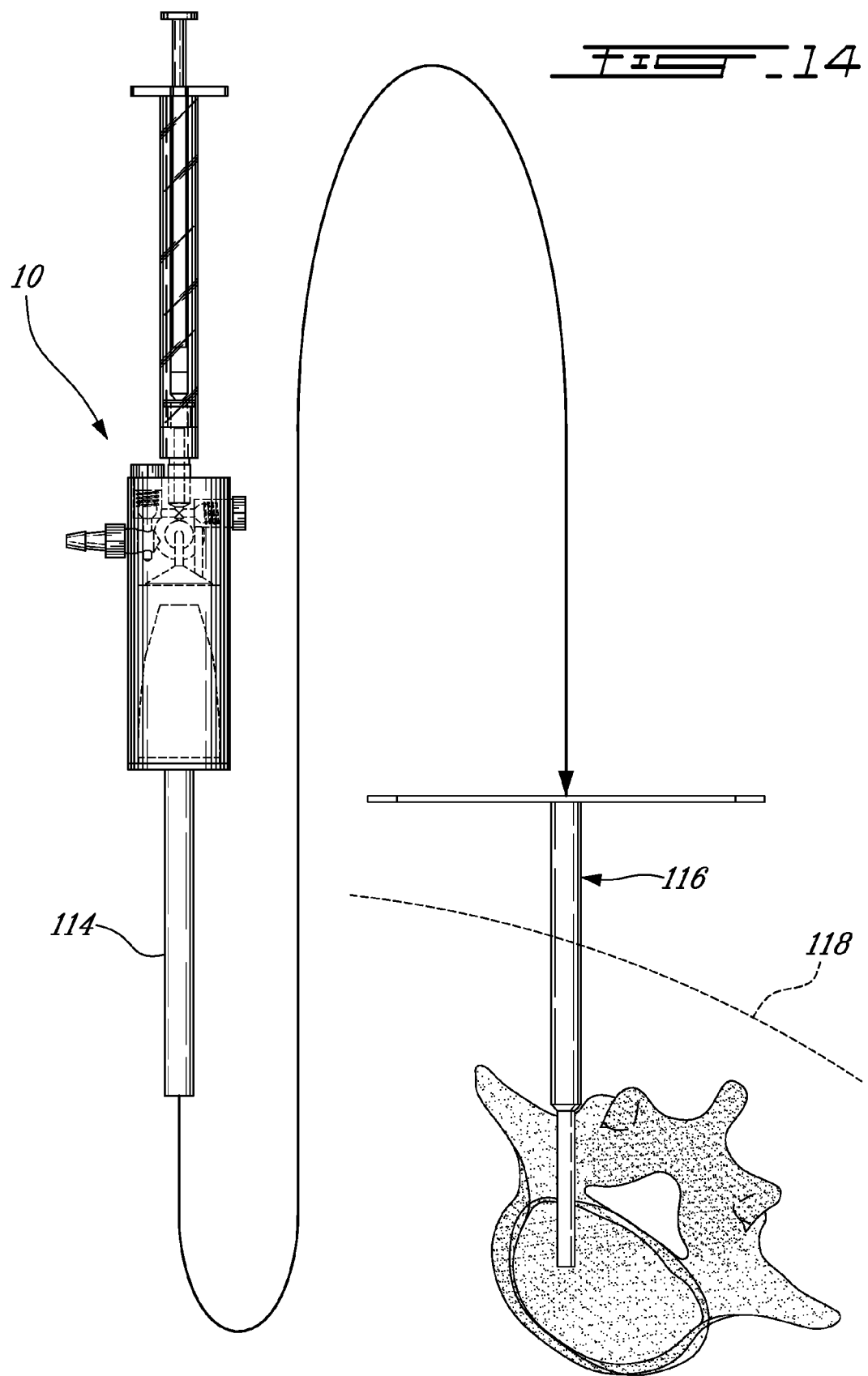

DEVICE FOR INJECTING HIGH VISCOSITY MATERIAL

CROSS-REFERENCE TO RELATED APPLICATIONS

This is a continuation of International Application No. PCT/CA2006/001487 filed Sep. 7, 2006, designating the United States, which itself claims priority on U.S. provisional application 60/714,343 filed Sep. 7, 2005, the specifications of both of which are incorporated herein by reference.

BACKGROUND OF THE INVENTION

1. Field of the Invention

The present invention relates to the field of injection biomechanics, and more particularly to a device for injecting a high viscosity material to a site within a patient.

2. Description of the Prior Art

Osteoporosis is caused by a gradual loss of bone minerals along with a progressive structural change of trabecular bone (increased porosity, loss of horizontal struts, etc.). Trabecular bone, therefore, loses density and strength and becomes more susceptible to so-called fragility fractures. Vertebral fragility fractures often occur, resulting in chronic pain, progressive deformity and possibly even neurological deficit or damage.

Percutaneous vertebroplasty is an emerging procedure used to strengthen mechanically incompetent vertebrae affected by osteoporosis. This procedure involves injection of viscous bone cement into the trabecular bone of the vertebra. The cement, once hardened, becomes a permanent reinforcement of the vertebral body and usually drastically diminishes the pain experienced by the patient. Injecting viscous materials into other tissues in the body is also known, for instance injecting viscous bone cement to mechanically augment the proximal femur, the metaphyseal regions around the knee or the distal radius. Or injecting a gel-like (generally softer) material into the intervertebral disc to replace the nucleus pulposus.

Most often a posterior percutaneous and transpedicular approach is used to access the vertebral body. The approach can be uni- or bipedicular. Alternative surgical approaches are posterolateral and intertransverse, with a direct lateral penetration of the vertebral body.

Percutaneous vertebroplasty has also been used to reinforce vertebral bodies weakened because of osteolytic spinal tumours (haemangioma, metastatic spinal tumours, etc.).

Percutaneous transpedicular vertebroplasty is generally performed with an approximately 15 cm long 8-gauge or 11-gauge Jamshidi bone biopsy needle, composed of a straight cannula with a T-handle and removable trocar. The trocar is used along with the cannula to pierce the cutaneous layers and the cortical bone of the vertebra so that the tip of the cannula can be positioned transpedicularly in the cancellous bone of the vertebral body. The trocar is then removed and bone cement is delivered through the cannula, usually under fluoroscopic guidance, into the trabecular bone of the vertebral body.

In order to uniformly infiltrate the vertebral body and avoid unwanted leakage, the bone cement needs to have a viscosity preferably more than 100 Pa*s, possibly even more than 300 Pa*s. Injecting low viscosity bone cement can cause cement leakage into the surrounding venous blood vessels, leading potentially to serious complications such as arterial blood pressure drop and/or lung embolism, possibly with fatal outcome. Immediate abortion of the procedure, if the complication is recognized timely, may limit the damage, but generally does not avoid it. Therefore, it is desirable for surgeons to work with relatively high viscosity bone cements to actually decrease, possibly even avoid, the potential risk of such complications occurring.

It is common practice for some surgeons to use multiple small volume syringes (i.e. 1 cc to 3 cc) capable of being generated by a surgeon using one hand, the pressure required to inject relatively high viscosity bone cement. However, even with the desired bone cement viscosity this method of treatment still has an elevated risk of cement leakage occurring due to the surgeon being distracted from the procedure at hand by the constant demand of changing the syringes. Still other disadvantages of working with multiple small syringes are that the procedure is time consuming, messy, and filling multiple small syringes ahead of time with cement may cause the syringe nozzle to clog.

In some cases involving high viscosity cement the procedure may have to be abandoned because the injection pressure becomes too great to be manually applied. The maximum obtained pressure generated one-handed with a standard 2 cc syringe is roughly in the order of 1700 kPa. Using a high viscosity cement implies that the majority of the injection pressure generated by the surgeon is required to overcome the friction of the cement in the cannula. The required injection pressure can easily reach 1900 kpa in the case of a 15 cm long 8-gauge cannula, and up to 6900 kPa in the case of a 15 cm 11 gauge cannula, which is well beyond the limit of what the surgeon can manually generate to inject cement with a standard syringe.

Methods and devices have been designed to provide sufficient pressure for injecting relatively viscous bone cements and/or provide sufficient volumes of cement but each with significant disadvantages.

For instance, some devices include hand lever pumps, or power screw designs making them large and bulky. Although these devices are able to generate the necessary pressures, they are unsuitable for mounting directly atop of a cannula due to existing weight constraints. Also, the use of larger devices is very cumbersome in a multi-level procedure requiring up to three or four units simultaneously. The sheer size of these devices makes them impractical to use. To solve the aforementioned problem, some devices that generate mechanical advantage have been connected to the cannula via a long, small diameter tubing. Unfortunately, the friction of the cement flowing through the long small diameter tube is relatively high and therefore much of the force generated by the devices is used to overcome the friction. Furthermore, the incorporation of a long and reasonably large diameter delivery tube to enable cement flow, and the much higher pressure requirements to overcome additional friction, dramatically limits the tactile feedback for the surgeon. This limitation is largely due to increased system compliance caused by higher pressures and longer tubing (i.e., the tactile feedback is less direct).

U.S. Patent Application Publication 2005/0070915 A1 by Mazzuca et al describes a device including a delivery tube extending outside the fluoroscopy radiation field for safely activating the movement of the bone cement into the patient while still taking into account the necessary pressure requirements. In the preferred embodiment the viscous material does not travel via the delivery tube, thus greatly reducing friction in the device. Furthermore, the delivery tube is said to be non-compliant in nature; however, in reality, the compliance disclosed as being present is still too great even at the values specified in the disclosure. A 10% change in volume under operating pressures of about 8274 kPa for a 2.5 mm diameter tube that is 60 cm long yields approximately ⅓ cc of extra cement. If the system is pressurized to 8274 kPa the compliance of the device can be extremely hazardous to the patient.

Accordingly, there is a need for a device for injecting a viscous material that addresses some or all of the aforementioned problems.

SUMMARY OF THE INVENTION

It is therefore an aim of the present invention to provide a device that provides mechanical advantage for injecting viscous material.

It is also an aim of the present invention to provide a device for injecting high viscosity material through a cannula into a site in a patient.

Therefore, in accordance with one aspect of the present invention, there is provided a device for injecting a high viscosity material into a cannula, comprising a container being non-compliant and having an outlet adapted to communicate with the cannula for transferring the high viscosity material thereto, a pressure applicator in fluid communication with the container, the pressure applicator defining a fluid flow path through which an incompressible fluid is displaceable, and a material-moving member interrupting the fluid flow path and defining an incompressible fluid receiving portion on one side thereof and a high viscosity material receiving portion on an opposed side, the incompressible fluid receiving portion being in communication with the fluid flow path of the pressure applicator and the high viscosity material receiving portion being in communication with the outlet of the container, the material-moving member being displaceable by a pressure of the incompressible fluid acting thereagainst to force the high viscosity material out of the high viscosity material receiving portion of the container and into the cannula.

In accordance with another aspect of the present invention, there is provided a device for injecting high viscosity material, comprising a non-compliant body, a material-moving member separating the non-compliant body into a first cavity having a first volume adapted to receive an incompressible fluid and a second cavity having a second volume adapted to receive a high viscosity material, the material-moving member being displaceable to vary the first and second volumes inversely proportionally, and a pressure applicator for displacing the incompressible fluid into the first cavity that displaces the material-moving member to increase the first volume and decrease the second volume, thereby ejecting the high viscosity material out of the non-compliant body.

In accordance with a further aspect of the present invention, there is provided a container for a device for injecting high viscosity material into a tissue of a patient, comprising a proximal end, a distal end defining an outlet adapted to communicate with a cannula, a flexible yet non-compliant bag received in the container and adapted to receive the high viscosity material, the bag having an opening connected to the distal end of the container in communication with the outlet thereof, the container adapted to receive a pressurized incompressible fluid surrounding the bag thereby collapsing the bag and forcing the high viscosity material therewithin through the outlet of the container.

In accordance with a yet another aspect of the present invention, there is provided a device for injecting high viscosity material into a tissue of a patient, comprising a non-compliant container having a proximal end defining an inlet, a distal end defining an outlet adapted to communicate with a cannula, a pressure applicator in fluid communication with the non-compliant container, the pressure applicator operable to generate a pressure build up of an incompressible fluid. The pressure applicator comprising a housing having a fluid inlet, a fluid outlet and a fluid flow path defined therebetween, at least one check valve in the flow path controlling the fluid flow, the fluid outlet in fluid flow communication with the container, and a power piston connected to the housing in fluid flow communication with the flow path, the power piston for generating mechanical advantage by building up pressure in the fluid flow path with an incompressible fluid being displaceable between a first and a second position, when displaced towards the second position the power piston creating a suction force drawing the incompressible fluid through the inlet, the check valve preventing a back flow through the outlet and back into the housing, when displaced towards the first position the power piston creating a pressure driving the incompressible fluid past the check valve out of the housing through the outlet and into the non compliant container. The device further comprising a material-moving member separating a fluid flow path between the non-compliant container and the pressure applicator into an incompressible fluid receiving portion and a high viscosity material receiving portion, the material-moving member being movable by the pressure exerted thereon by the incompressible fluid within the incompressible fluid receiving portion toward the outlet of the non-compliant container, thereby forcing the high viscosity material out of the high viscosity material receiving portion and into the cannula.

BRIEF DESCRIPTION OF THE DRAWINGS

Reference will now be made to the accompanying drawings, showing by way of illustration a preferred embodiment thereof, and in which:

FIG. 6 is a cross-sectional view of the device in accordance with a second particular embodiment of the present invention, showing the container connected to the pressure applicator by way of an extension line;

FIG. 14 is an exploded view of the device in accordance with a ninth embodiment of the present invention, shown in relation to a cannula-type device.

DESCRIPTION OF THE PREFERRED EMBODIMENTS

Figure 1:
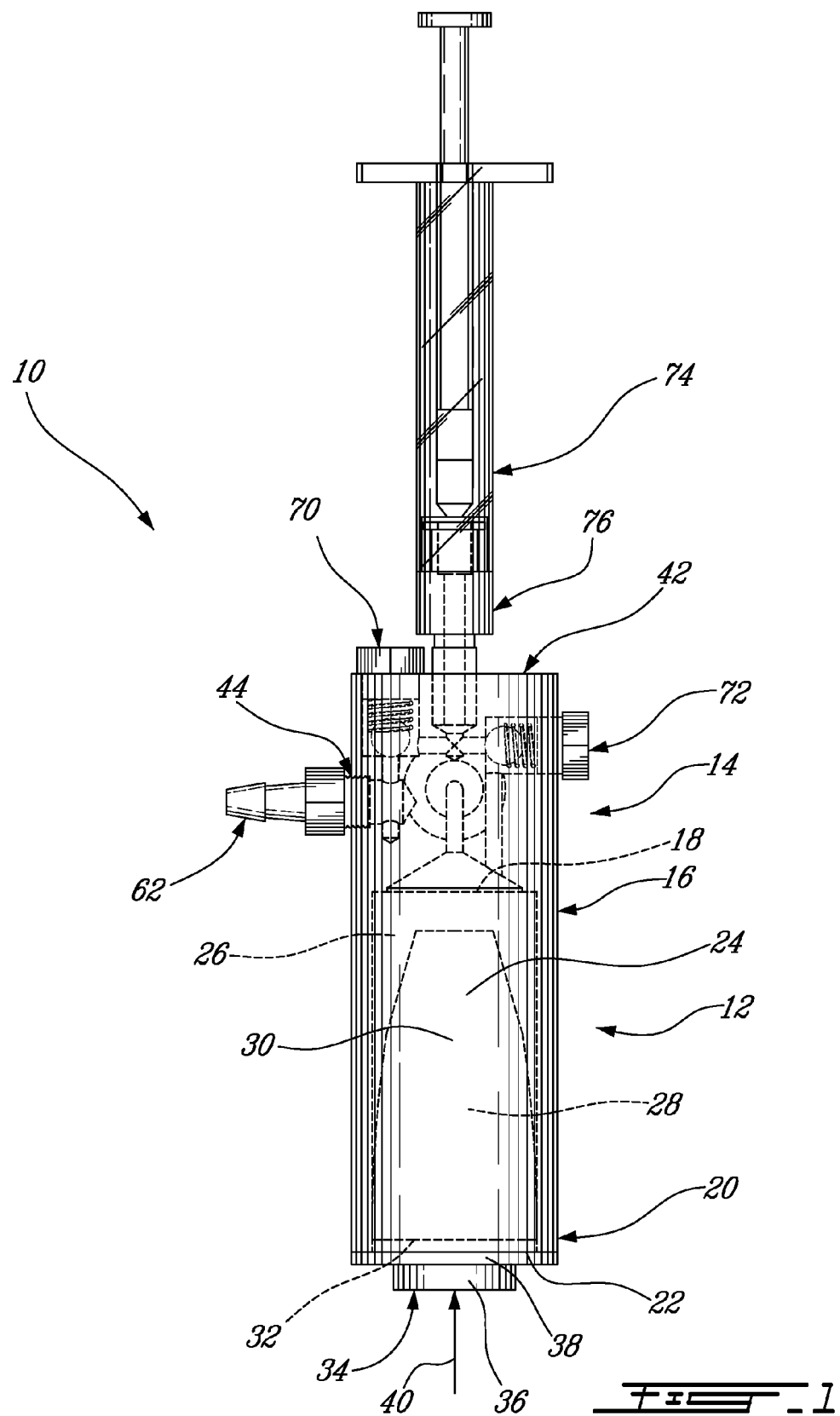
FIG. 1 is a perspective view of a device comprising a container and a pressure applicator for injecting viscous material in accordance with a first particular embodiment of the present invention.

FIGS. 1 through 4 illustrate a first particular embodiment of a device capable of generating mechanical advantage for injecting a viscous material into a tissue. In general, the device designated by reference numeral 10, is shown comprising a non-compliant container 12 coupled to a pressure applicator 14. The container 12 is adapted to communicate with a cannula (not shown) seated at the delivery site of a patient, often in the radiation field of a fluoroscope. The device 10 is adapted to contain two materials, the viscous material to be injected into the patient and an incompressible fluid to act on the viscous material for providing mechanical advantage to the operator.

More specifically, the expression "viscous material" and/or high viscosity material is used herein to refer to a material having a viscosity significantly greater than that of the incompressible fluid, and preferably at least 100 Pa*s. The viscosity of the viscous material may be between 100 and 500 Pa*s, but potentially may be even higher. The viscous material includes among other materials Polymethylmethacrylate (PMMA) cement, Calcium Phosphate cement, physical or chemical gels (e.g., Polyethylenglycol, Polyvinylalcohol) and the incompressible fluid is preferably a sterile, non-toxic, incompressible low viscosity fluid such as distilled water or physiologic saline solution. Note, the low viscosity of the incompressible fluid is important to both reduce the friction in the device 10 but also to facilitate the deaeration of the fluid during assembly of the injection device, as will be discussed furtheron.

The device 10 can inject viscous material into any existing cavity or virtual cavity, the latter being formed during injection. More specifically, the injection procedure is performed for the purpose of either augmenting tissue or substituting tissue. Augmenting tissue results in more mechanical strength and more volume. Substituting tissue is carried out because of a loss of tissue due to a physiologic or pathologic process (e.g., age, degeneration, infection, trauma), or due to surgical removal.

One possible application is the injection of a relatively viscous bone cement into a vertebral body for augmentation (see FIG. 14), while another is the substitution of intervertebral disc tissue, more specifically the nucleus pulposus, with a viscous gel. Yet other applications are the injection of bone cement for mechanical augmentation into other bones of a patient such as the proximal femur, the metapyseal longbone areas around the knee, the distal radius, and others The container 12 is preferably cylindrical in shape having a proximal end 16 defining an inlet 18 and a distal end 20 defining an outlet 22. The container 12 has a material-moving member 24 defining a first cavity 26 in communication with the inlet 18 and a second cavity 28 in communication with the outlet 22. The first cavity 26 is adapted to receive the incompressible fluid and the second cavity 28 is adapted to receive the viscous material.

In one particular embodiment, the material-moving member 24 is a flexible non-compliant bag 30 that is adapted for inclusion in the container 12 as depicted in FIGS. 1 to 4. The term flexible is used to mean supple, displaceable and deformable while the term non-compliant is used to mean resistant and non-stretchable. Thus, for example, flexible and non-compliant refers to a bag that is made from not elastic material that, upon being completely filled, demonstrates a sharp pressure rise while assuming a specific predefined shape and dimension. Thus, the second cavity 28 is defined as the space enclosed by the bag 30 and the first cavity 26 is defined as the space surrounding the bag 30 in the container 12. The bag 30 defines an opening 32 that is fixed about a mouthpiece 34. The mouthpiece 34 comprises a cylindrical body 36 and flange 38 and defines a central bore 40 therethrough for communicating with the opening 32 of the bag 30. The flange 38 is integral to the body 36 and has an outside diameter substantially the same as the outside diameter of the cylindrically shaped container 12. The mouthpiece 34 is adapted to mate with the container 12 when the bag 30 is inserted therein. More specifically, the mouthpiece 34 is threaded into the distal end 20 of the container 12 such that the flange 38 abuts the outlet 22.

Figure 5A:
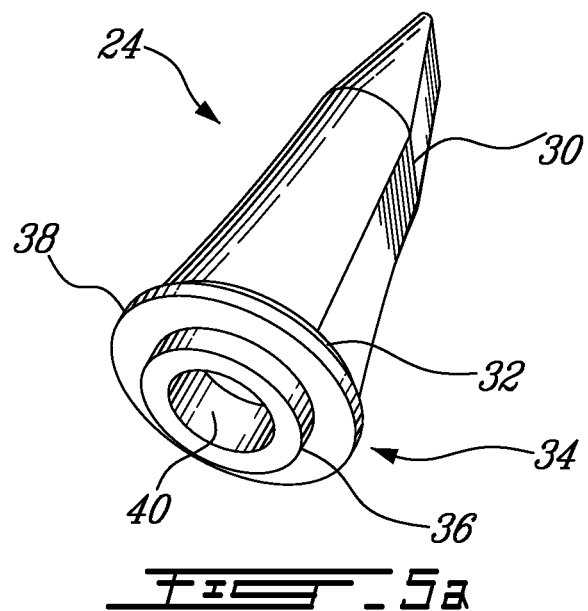
FIG. 5a is a perspective view of one embodiment of a flexible bag of the device of FIG. 1.
Figure 5B:
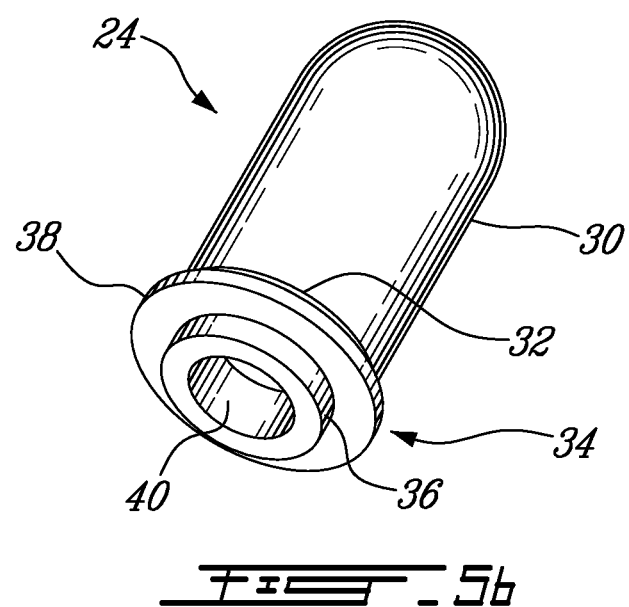
FIG. 5b is a perspective view of another embodiment of a flexible bag of the device of FIG. 1.

FIGS. 5a and 5b show two respective embodiments of the bag 30 fixed to the mouthpiece 34. One advantage of the bag 30 being detachable from the container 12 lies in that the viscous material (i.e. bone cement) can be pre-mixed in a simple, clean manner without the hassle of manipulating the entire device 10. Possibly even the bag can be shipped prefilled with the material, or components thereof, allowing for mixing the cement directly in the bag. Thus, in this embodiment the bag 30 and mouthpiece 34 are removed from the container 12, are prefilled or filled with material on site, and then re-attached when it is time to inject the material to the desired site.

The embodiment of the bag 30 illustrated in 5a is designed to facilitate the extrusion of the viscous material by avoiding any possible pinching off at the mid section. Furthermore, the bag 30 of FIG. 5a may allow for easier deaeration of the incompressible fluid within the first cavity 26. The bag illustrated in 5b is an example of the many possible shapes that could be used for this application.

The bag 30 acts as a material-moving member distinctly separating the incompressible fluid and the viscous material but with no moving mechanical parts that would have friction at the inside walls of the container 12. The bag 30 is very pliable to maximize the tactile feedback to the surgeon and thus improve the surgeon's ability to accurately control cement flow. The bag 30 is thin walled but with adequate strength and is preferably made of polyurethane, or silicone or any non-toxic biocompatible material.

The container 12 may be made of polycarbonate. Of course many other suitable materials exist that can sustain the pressures generated within the container 12. Advantageously, the container 12 can supply a sufficient volume of viscous material to complete injection of the necessary amount of high viscous material in one application without needing to be refilled. For example, in the case of injecting bone cement in the lumbar region, the container 12 can supply at least the generally required 10 cc of bone cement in one application.

FIGS. 1 to 4 show the pressure applicator 14 of the device 10 adjacent to the proximal end 16 of the container 12 mounted in fluid communication therewith. Generally, the pressure applicator 14 uses an incompressible fluid to build up pressure to generate mechanical advantage for injecting the relatively high viscosity material. The pressure applicator 14 pumps the incompressible fluid into the container 12 thereby forcing the relatively high viscous material through the outlet 22 into the cannula. More specifically, the incompressible fluid is injected into the first cavity 26 of the container 12 until sufficient pressure builds up on the material-moving member 24 causing the latter to undergo displacement. Thus, the injection of incompressible fluid causes the first cavity 26 to increase in volume and the second cavity 28 to decrease in volume thereby forcing the contents of the second cavity 28 to exit the outlet 22.

In FIGS. 1 to 4 the pressure applicator 14 and the container 12 are integrally joined to form the device 10. It is to be understood that the pressure applicator 14 and the container 12 may be provided as separate entities interconnected to perform a desired function or may be integral thereby forming a single physical unit.

FIG. 6 illustrates a second embodiment where the container 12 and the pressure applicator 14 may be connected with an extension line provided as a small inner diameter tube 41 of low compliance that is less than 1 mm in diameter, with thick walls. This embodiment allows the pressure applicator to be removed from the radiation field while maintaining the tactile feedback of the device. The container 12, containing the viscous cement, remains at the closest possible distance from the injection site. As compliance (i.e. of the extension line 41) becomes a greater concern with this embodiment, it is important to have the smallest possible inner diameter for the tube 41 so that the surface tension acting on the tube for any given pressure within the tube is minimal and so that the wall thickness in relation to the tube's inner diameter can be sufficiently larger to minimize compliance.

Figure 2:
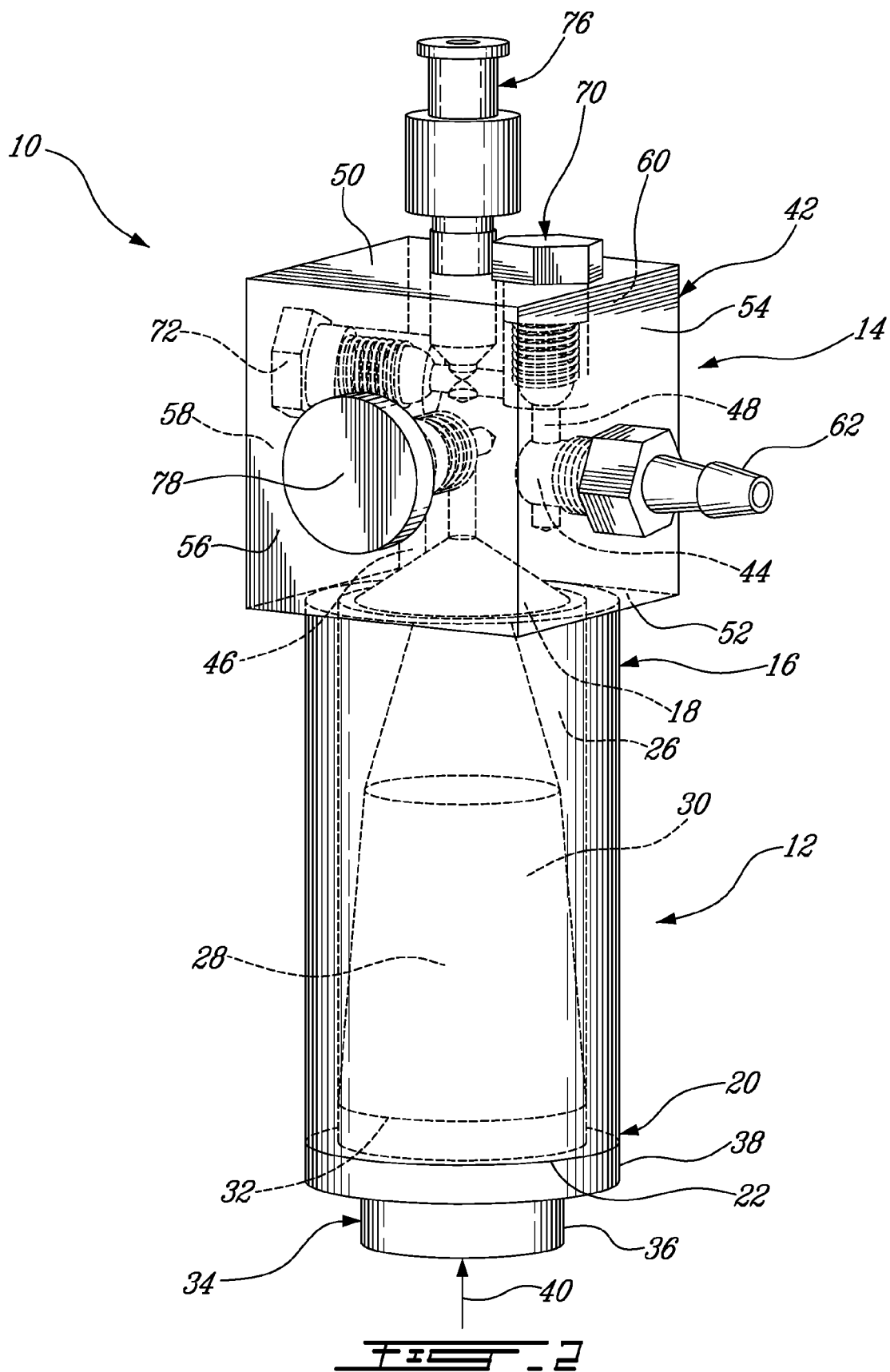
FIG. 2 is another perspective view of the device shown in FIG. 1.
Figure 3:
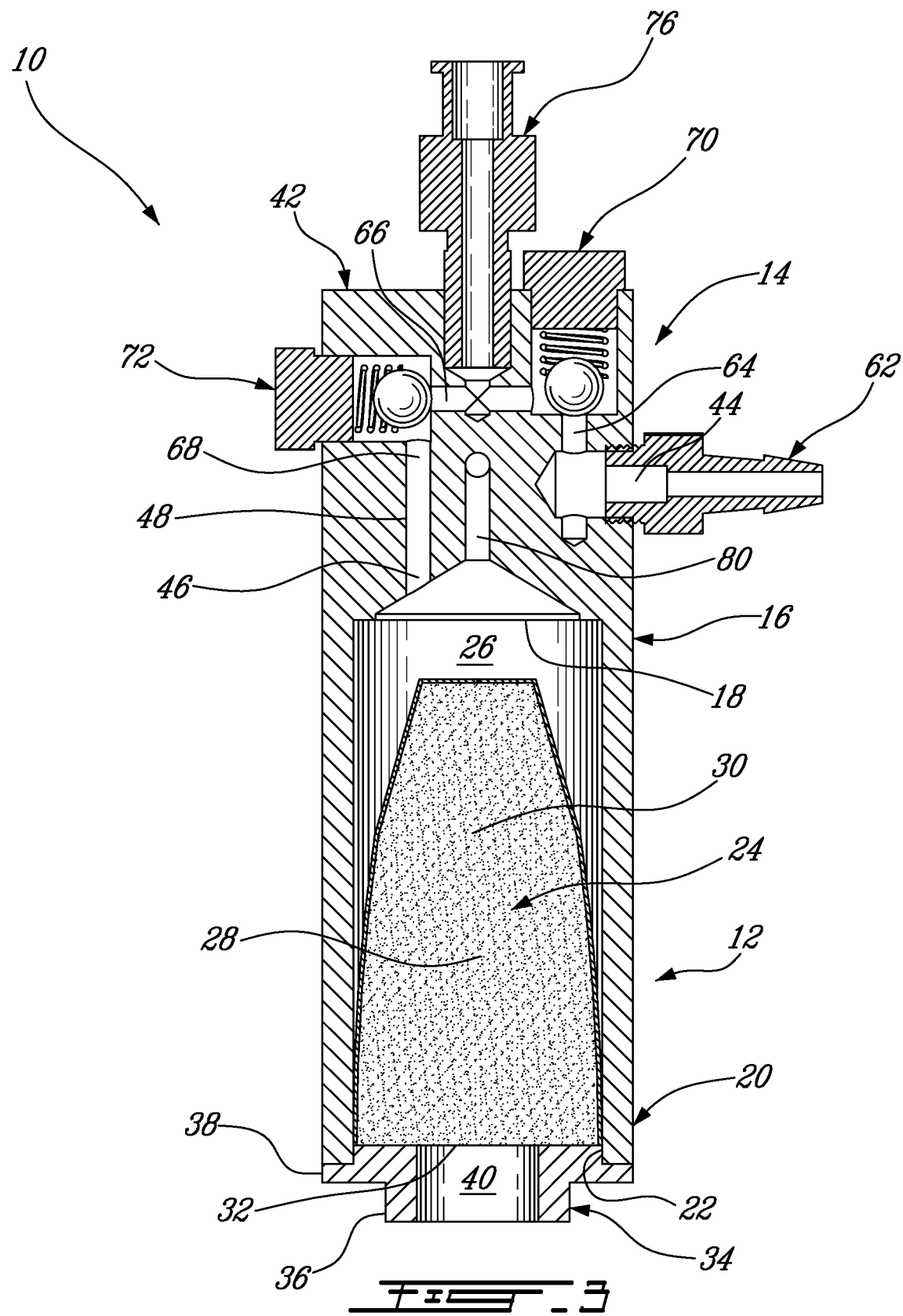
FIG. 3 is a sectional view of the device taken along cross-sectional lines 3-3 of FIG. 2.

As best seen in FIGS. 2 and 3, the pressure applicator 14 comprises a housing 42 having a fluid inlet 44, a fluid outlet 46 and a fluid flow path 48 defined therebetween. In the first particular embodiment illustrated in FIGS. 1 to 4 the housing 42 is depicted as being rectangular, however, it should be understood that the housing may take on many other shapes or forms. For exemplary purposes, the housing 42 will be described as having a top surface 50, a bottom surface 52 and four side surfaces 54, 56, 58 and 60 respectively.

Specifically, the fluid inlet 44 is disposed within side surface 54 in communication with a fluid supply line connector 62. The supply line connector 62 is exemplified as a male type fitting adapted to receive a supply line from a reservoir. For example, a gravity feed reservoir may be used such that the incompressible fluid enters the fluid inlet 44 with sufficient head pressure generated by the height of the reservoir. Such a reservoir filled with a sterile solution or fluid solution such as an infusion bag or water or any physiological fluid is commonly found in most operating rooms. Alternatively, this pressure of the incompressible fluid may be generated by suitable mechanical means. In another example, the fluid supply line connector 62 may be a female luer connector allowing for the connection of a syringe containing the incompressible fluid to act as the reservoir. Advantageously, in both of the above examples the device 10 is compatible with an already existing apparatus, making it simple in design.

Still referring to FIGS. 1 through 4, the fluid outlet 46 of the pressure applicator 14 is disposed in the bottom surface 52 for communicating with the inlet 18 of the container 12. The flow path 48 is defined by three interconnected, orthogonally oriented tubes 64, 66 and 68.

The pressure applicator 14 further comprises a first and a second check valve 70 and 72 respectively in the flow path 48 controlling the fluid flow. Preferably, tube 64 extends from the fluid inlet 44 to the first check valve 70, tube 66 extends from the first check valve 70 to the second check valve 72, and tube 68 extends from the second check valve 72 to the fluid outlet 46. The first check valve 70 protrudes from the top surface 50 of the housing 42 while the second check valve 72 protrudes from side 58 thereof.

The first and second check valves 70, 72 are one-way valves installed to permit the flow of fluid in one direction. More specifically, the first check valve 70 acts to prevent fluid back flow out of the fluid inlet 44 and similarly the second check valve 72 acts to prevent the intake of fluid into the flow path 48 through the fluid outlet 46.

Now referring to FIG. 1, it can be seen that the pressure applicator 14 further comprises a power piston 74 connected to the housing 42 in fluid flow communication with the flow path 48 between the first and the second check valves 70, 72. More specifically, the pressure applicator 14 has a sealing connector 76 adapted for receiving the power piston 74 (FIGS. 1-4). The sealing connector 76 is in fluid communication with tube 66 between the first and second check valves 70, 72 and protrudes from the top surface 50 of the housing 42. The sealing connector 76 is a female luer-lock type fitting. Any standard syringe can be used as a power piston 74, however, the greatest mechanical advantage will be gained by using the smallest possible diameter syringe as the force required to pump same is reduced, or the maximum pressure obtained is increased. The pressure applicator 14, using a 1 cc syringe, has been recorded as generating a pressure up to 3792 kPa. The force applied to the power piston 74 results in a pressure that is transmitted undiminished via the incompressible fluid to the distant diaphragm. Notably, in said system the pressure required for injecting a viscous material is independent of the geometry of the container 12. It should be noted however, that the power piston 74 may be built into the device 10 instead of being provided as a standard syringe.

The power piston 74 is displaceable between a first and a second position, the first position being at maximum compression as illustrated in FIG. 1 and the second position being the most extended. When displaced towards the second position, the power piston 74 creates a suction force drawing the incompressible fluid through the fluid inlet 44 past the first check valve 70. Meanwhile, the second check valve 72 prevents a back flow of the fluid from the first cavity 26 into the housing 42 through the fluid outlet 46. When displaced towards the first position the power piston creates a pressure driving the incompressible fluid past the second check valve 72 out of the housing 42 through the fluid outlet 46, while the first check valve 70 prevents the ejection of fluid back out of the housing 42 through the fluid inlet 44. Once the flow stops, the second check valve closes, thus trapping the fluid in the first cavity 26. Repeating this process, i.e. pumping the power piston 74, allows the operator to pump larger volumes of the incompressible fluid at similar pressures.

Notably, the pressure applicator 14 may include a return spring (not shown) to "automatically" reload the power piston 74. The addition of the return spring allows for one-handed operation of the device. Freeing the second hand of a surgeon allows for the possibility of operating two devices at once, thus decreasing surgery time.

Moreover, a cable inside a sheath (not shown), similar to a bicycle cable, can be attached to the power piston 74 for actuation thereof from a distance. This is advantageous for surgeons that prefer to keep their hands out of the radiation field. The cable has no or very little compliance and maintains the sensitivity feedback of the injection of the device 10.

Figure 4:
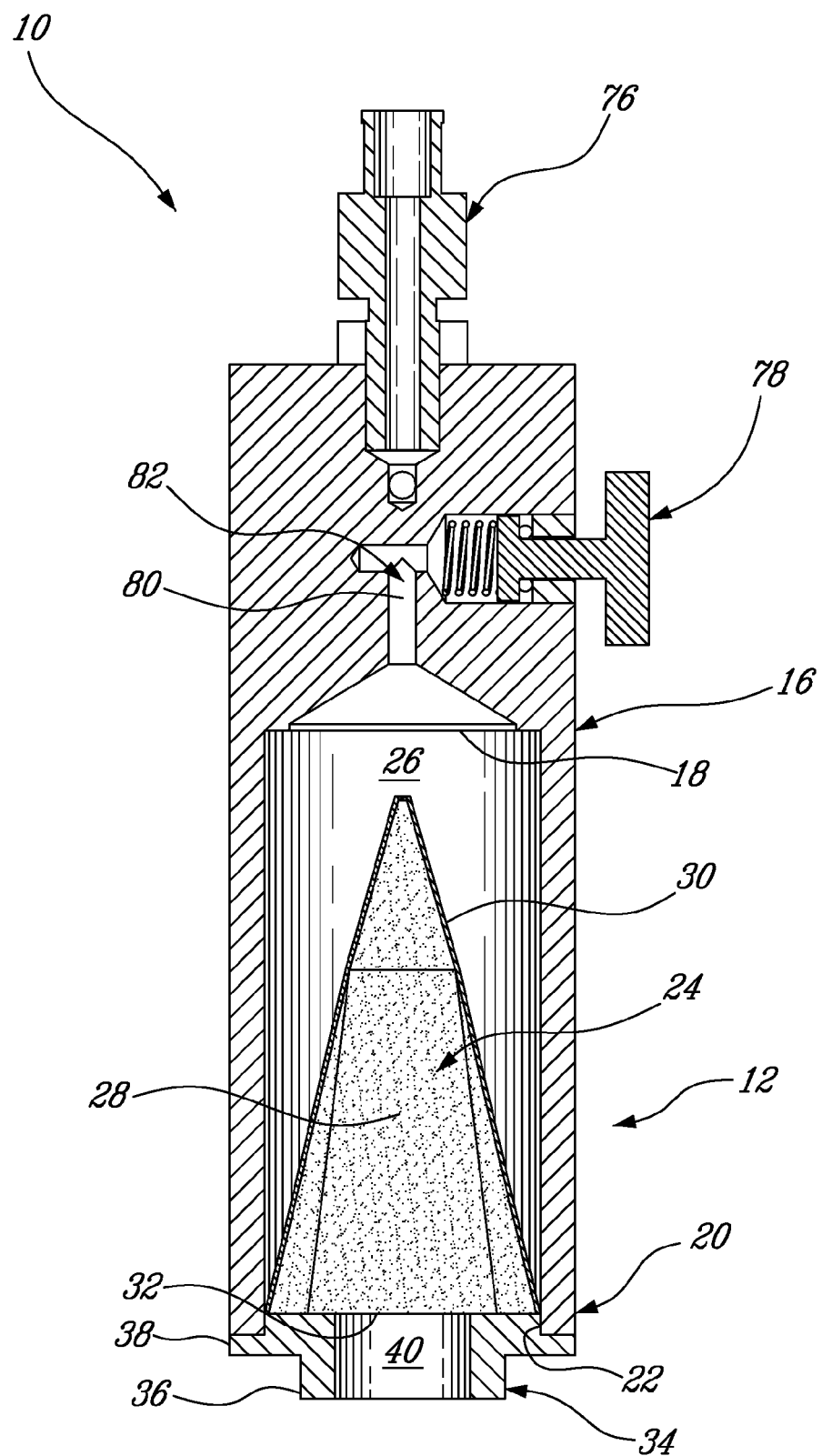
FIG. 4 is a sectional view of the device taken along cross-sectional lines 4-4 of FIG. 2.

In addition, the pressure applicator 14 preferably includes safety features. One possible safety feature that may be provided on the device 10 is a pressure relief valve 78 (see FIG. 4 for example) for equalizing the pressure inside the device 10, and more particularly inside the first cavity 26 of the container 12, with atmospheric pressure. Referring particularly to FIGS. 2 and 4, the pressure relief valve 78 is shown to be in fluid communication with the container 12, and more specifically with the first cavity 26 thereof in the location of significant pressure build-up. The pressure relief valve 78 is shown as protruding from side surface 56 of the housing 42 and connected to a tube 80 defining a pressure relief path 82. The pressure relief path 82 is independent from the fluid flow path 48 defined in the housing 42. The tube 80 extends within the housing 42 such that it communicates with the inlet 18 of the container 12 at one end and with the pressure relief valve 78 at the other end independently from the interconnected tubing configuration previously described.

Figure 7:
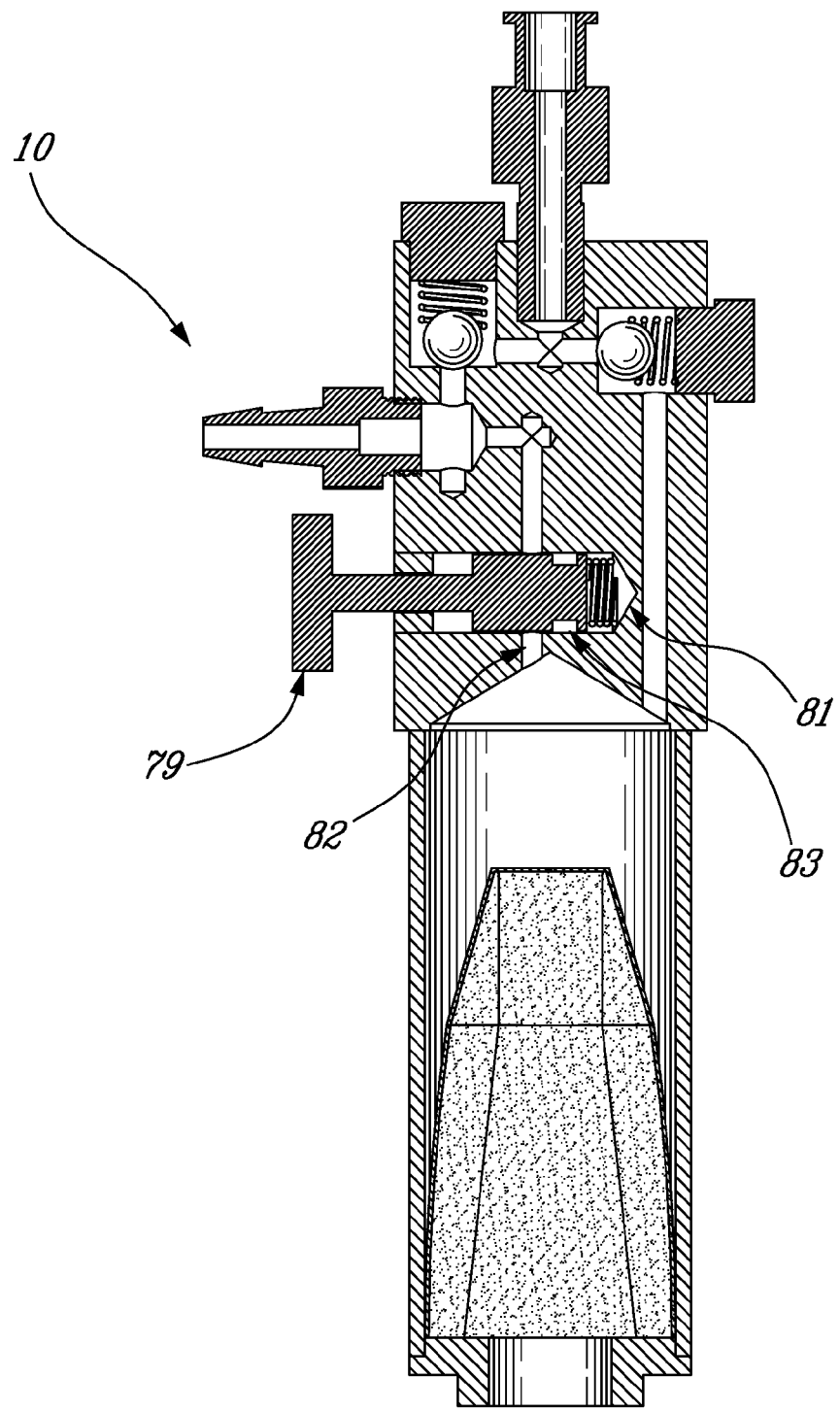
FIG. 7 is a cross-sectional view of the device in accordance with a third particular embodiment of the present invention, showing a fail safe switch.

Therefore, during a surgery involving the injection of a viscous material into a site of a patient using device 10, a surgeon can quickly actuate the pressure relief valve 78 to allow for immediate and complete relief of pressure on the viscous material so that all flow is terminated in the fastest possible time span. Alternatively, the pressure relief valve can be constructed to be substantially fail-safe. FIG. 7 illustrates a third particular embodiment of the device 10 including a fail safe switch such as a "dead-mans switch" that the surgeon must hold closed to operate the device 10 and release to remove the pressure. More particularly, the fail-safe switch includes a pin portion 79 and a spring 81. When the fail-safe switch is depressed, the volume of incompressible fluid builds up in the container 12 and the pin portion 79 blocks any back flow from occurring. Upon release of the fail-safe switch, the spring 81 pushes the pin portion 79 outwardly thereby aligning a channel 83 defined therein with the pressure relief path 82 allowing the incompressible fluid to flow out of the first cavity 26 of the container 12. Such a fail-safe switch is commonly referred to as a piston valve or trumpet valve in the art.

Furthermore, as the device 10 is based on the principle of using an incompressible fluid, it is desirable to purge or de-air the device prior to intaking any incompressible fluid. The pressure relief valve 78 can help purge the device 10 of any trapped air. An effective method of purging the remaining air is by drawing the power piston 74 into the second position and then activating the pressure relief valve 78 and pressing the power piston 74 simultaneously to force the air or/and any unwanted fluid out of the system.

Another safety feature that may be included as part of the device 10 is a suction port (not shown). Similarly to the pressure relief valve 78, the suction port could be provided on the housing 42 such that it independently communicates with the first cavity 26. The suction port enables the creation of a negative pressure by way of a vacuum connection or via a syringe. Vacuum can help to overcome compliance of the bone cement itself due to air entrainment during the mixing process. Entrapped air can be compressed and thus store energy in the pressurized cement. The negative pressure created by the suction will quickly de-pressurize the cement. In addition, a negative pressure in the device 10 could potentially suck viscous material already injected into a site in a patient back into the cannula and into the container 12. Such a function is greatly desirable for the surgeon to help decrease the amount of cement leakage, occurring as the result of too much cement injected into a site.

Yet another safety feature that can be included with the device 10 is a pressure gauge 71. The pressure gauge 71 is placed along the flow path 48 after the second check valve 72. Once the pressure in the device 10 is sufficiently high enough to move the viscous material, the pressure tends to drop; thus, it is advantageous for the surgeon to be provided with this information by way of a pressure gauge 71. In addition, by knowing the pressure required to force cement out of the cannula, the surgeon can determine the magnitude of the viscosity of the viscous material and determine the ideal moment to commence injection.

Figure 8:
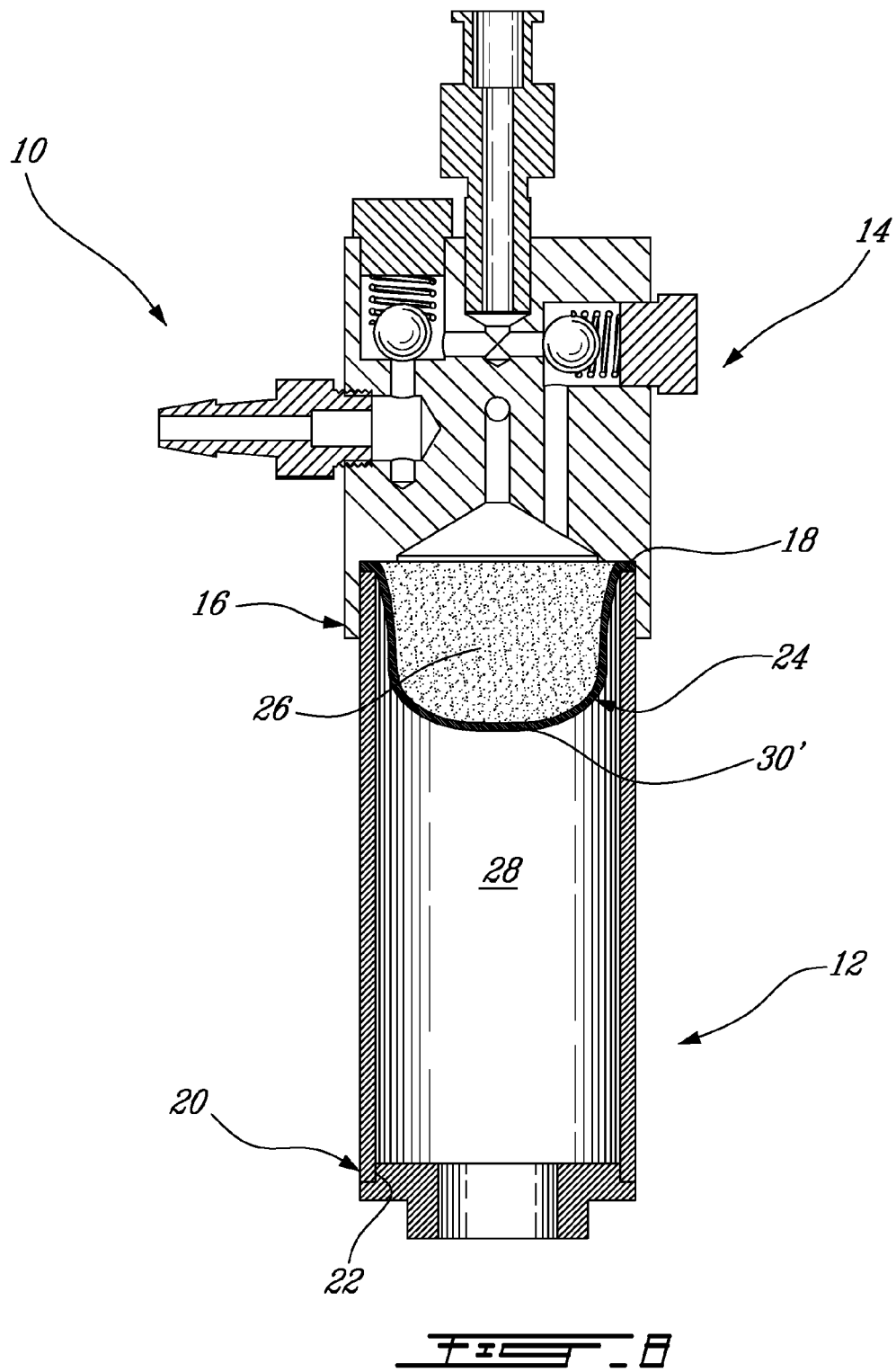
FIG. 8 is a cross-sectional view of the device in accordance with a fourth particular embodiment of the present invention, showing a flexible membrane in an expanded configuration.

Now referring to FIG. 8, a fourth particular embodiment of the device 10 is illustrated. Similar reference numerals have been employed to identify like features. This embodiment differs from the first presented embodiment in that, rather than having a flexible non-compliant bag, affixed to the mouthpiece 34, the material-moving member is provided as a soft and stretchable membrane to the inlet 18 at the proximal end 16 of the container 12. The membrane 30' of the second embodiment is adapted to cover the inlet 18 when not under pressure, thus the first and second cavities 26, 28 of the container 12 are defined when pressure is applied against the membrane 30'. The membrane 30' may therefore be elastically extendable by the pressure of the incompressible fluid acting thereagainst. In this embodiment, the first cavity 26 is defined as the space enclosed by the extended membrane 30' and the second cavity 28 is defined as the space surrounding the extended membrane 30' in the container 12. It remains that the first cavity 26 is adapted to receive the incompressible fluid and the second cavity 28 is adapted to receive the viscous material. Notably, a similar membrane 30' is shown in the embodiment of FIG. 6.

Figure 9:
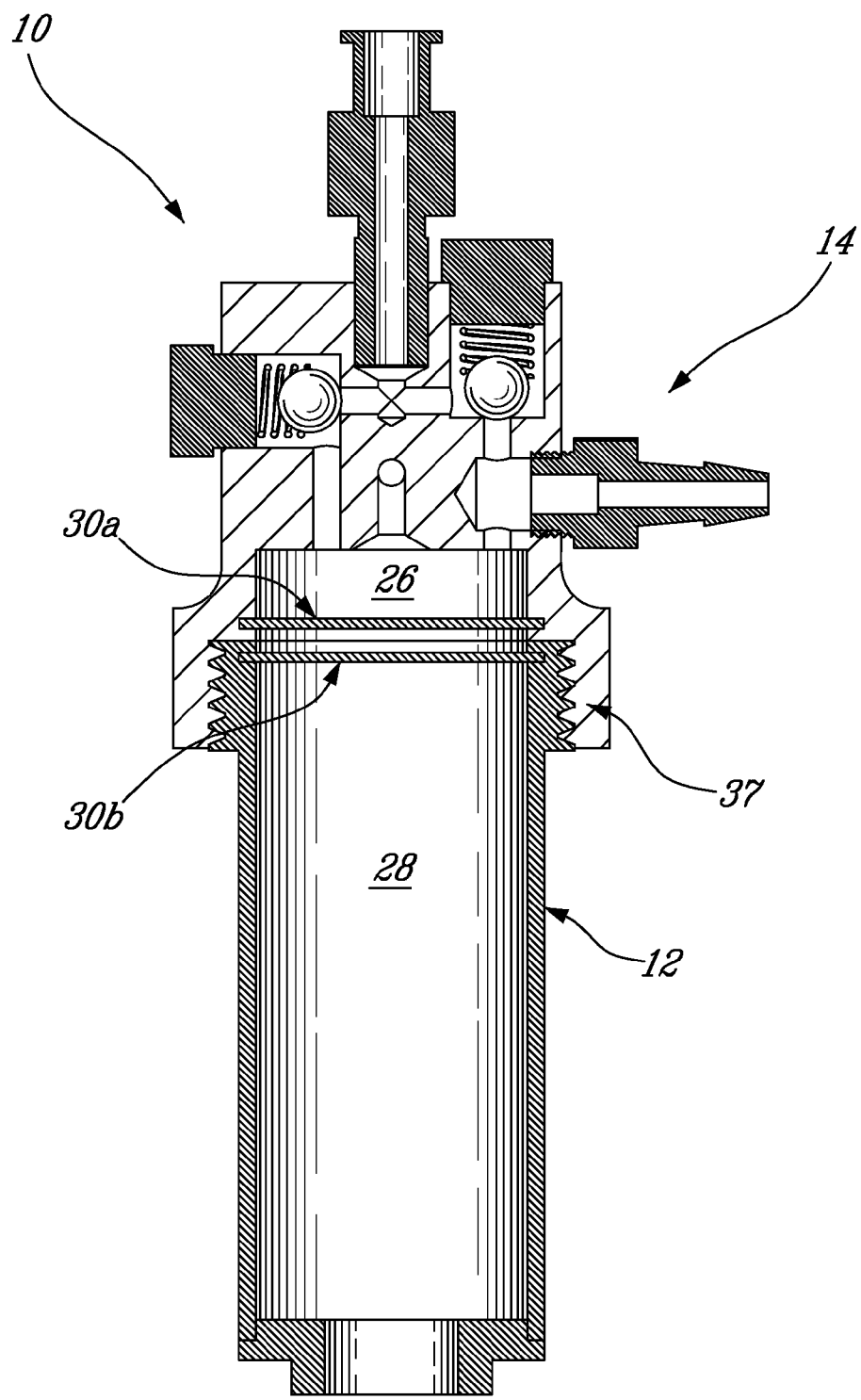
FIG. 9 is a cross-sectional view of the device in accordance with a fifth particular embodiment of the present invention, showing a flexible double membrane.

FIG. 9 illustrates a fifth embodiment of the device 10. Similar reference numerals have been employed to identify like features. In this embodiment the material-moving member is provided as a flexible double membrane identified as 30a and 30b. It can be seen that the flexible membrane 30a is attached to the pressure applicator 14 thereby defining the first cavity 26 adapted to receive the incompressible fluid therein. The flexible membrane 30b is attached proximal to, or at the inlet 18 of, the container 12, thereby defining the second cavity 28 adapted to receive the viscous material in the container 12.

In operation, the pumping of the power piston 74 (not shown in FIG. 9) will build up a volume of incompressible fluid in the first cavity 26 that will cause the flexible membrane 30a to expand. As the flexible membrane 30a expands, it will push against the flexible membrane 30b thereby causing the latter to apply a pressure against the viscous material in the second cavity 28. Thus, the more incompressible fluid that is pumped into the first cavity 26, the more viscous material will be pushed out of the container 12. Notably, the first cavity 26 expands in volume while the second cavity 28 decreases in volume (i.e. the overall volume within the container 12 remains constant, but the ratio of the volume of the first cavity 26 to the volume of the second cavity 28 varies).

Still referring to FIG. 9, it can be seen that the container 12 is attached to the pressure applicator 14 via a threaded coupling 37; however other examples include a quarter turn lock or a sliding lock in the shape of a dove tail. This embodiment is particularly advantageous because the container 12 can be detached from the pressure applicator 14 without exposing the incompressible fluid and viscous material contained in each.

Figure 10:
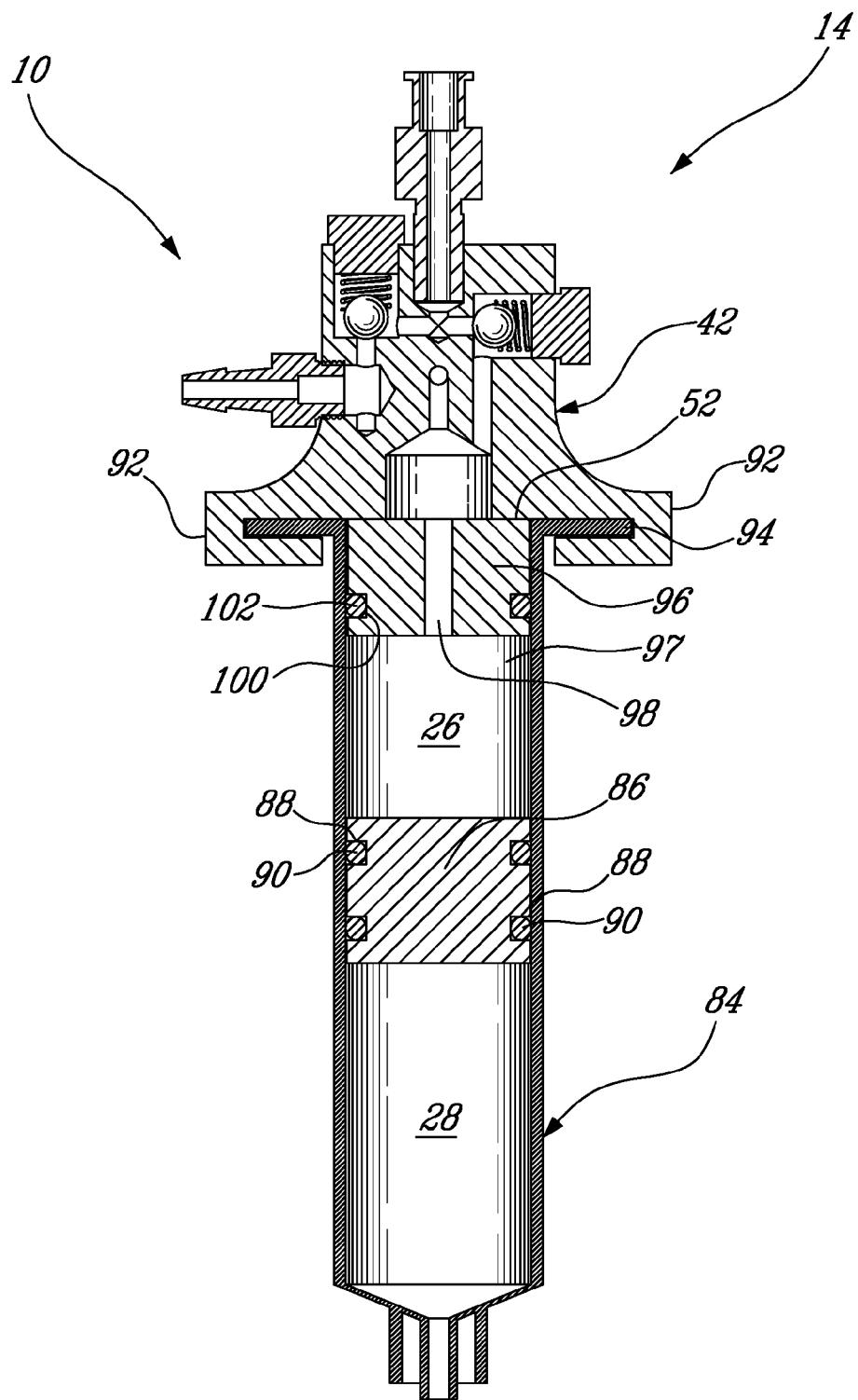
FIG. 10 is a cross-sectional view of the device in accordance with a sixth embodiment of the present invention.
Figure 11:
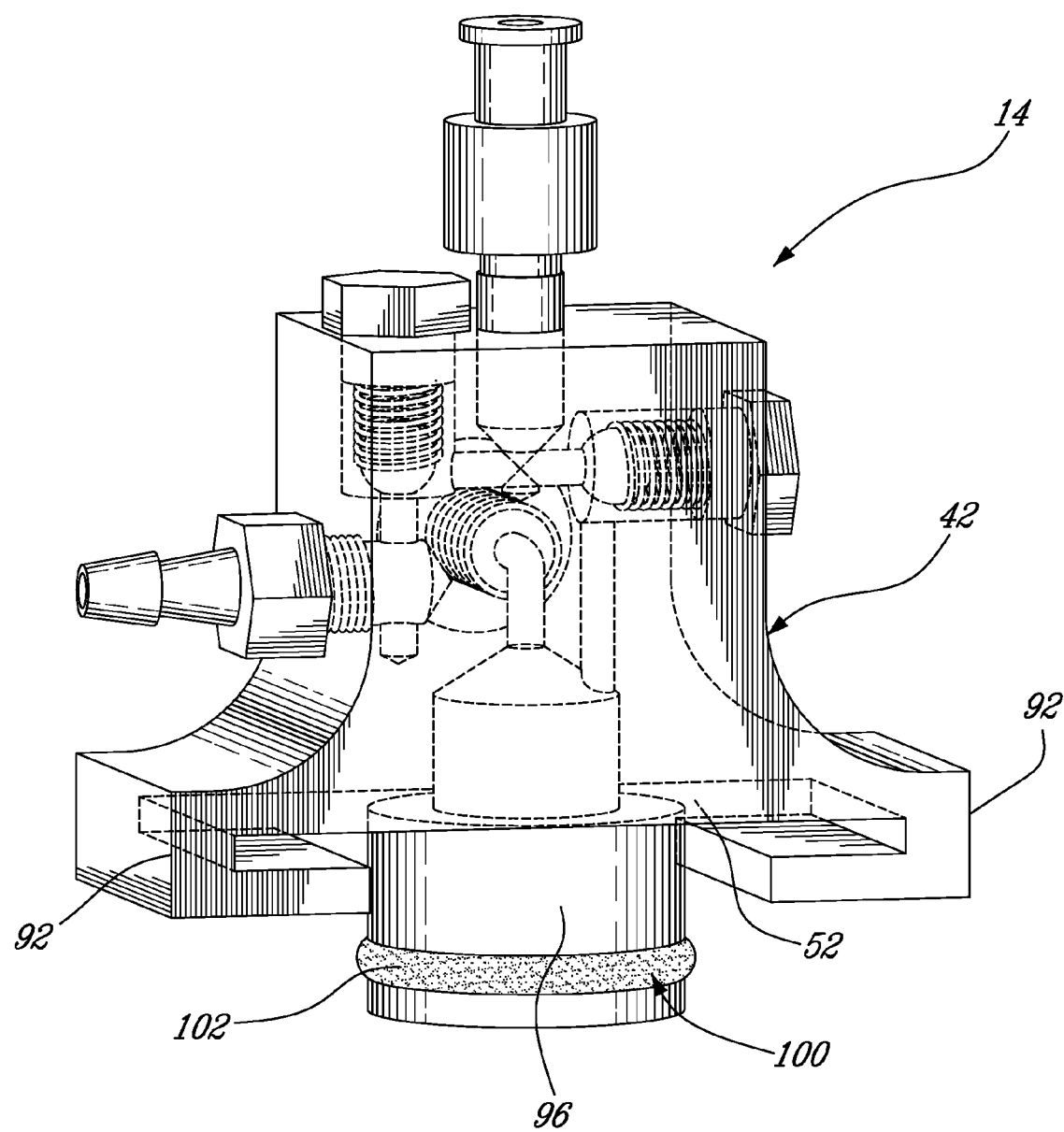
FIG. 11 is a perspective view of the pressure applicator of FIG. 10.

FIGS. 10 and 11 illustrate a sixth embodiment of the device 10. Similar reference numerals have been employed to identify like features. The sixth embodiment differs from the first presented embodiment in that the pressure applicator 14 is provided as a separate unit retrofitted with a standard ("off the shelf") syringe container 84. In this application the syringe container 84 takes the place of the container 12 of the preferred embodiment. More specifically, the syringe container 84 has a floating plunger 86 as the material-moving member 24 for defining the first and second cavities 26 and 28 respectively. Notably, the plunger 86 defines a pair of circumferential notches 88 with respective o-rings 90 for creating a seal between the floating plunger 86 and the syringe container 84. The housing 42 of this embodiment is retrofit with a pair of opposed hooks 92 for mating with the flange 94 of the syringe container 84. The housing 42 also includes a cylindrical portion 96 downwardly extending from the bottom surface 52 for insertion into the bore 97 defined at the proximal end of the syringe container 84. The cylindrical portion 96 defines a central bore 98 in communication with the fluid outlet 46 of the pressure applicator 14. The cylindrical portion 96 defines a circumferential notch 100 housing an o-ring 102 for making the joint between the cylindrical portion 96 and the syringe container 84 fluid-tight.

A method of injecting viscous material with this embodiment entails moving the plunger of the syringe to the distal end thereof before attaching the pressure applicator thereto. Next, the viscous material is injected retrograde into the syringe container 84 while it is of sufficiently low viscosity, until the moving floating plunger 86 reaches the proximal end thereof. At this time, the pressure applicator 14 can be attached to the proximal end via hooks 92 and the device 10 can be attached to the proximal end of a cannula. The device is then purged of air as previously described and primed with incompressible fluid at which point the surgeon can begin generating mechanical advantage to force the viscous material, which potentially has become substantially more viscous with time, out of the syringe into the cannula.

Figure 12:
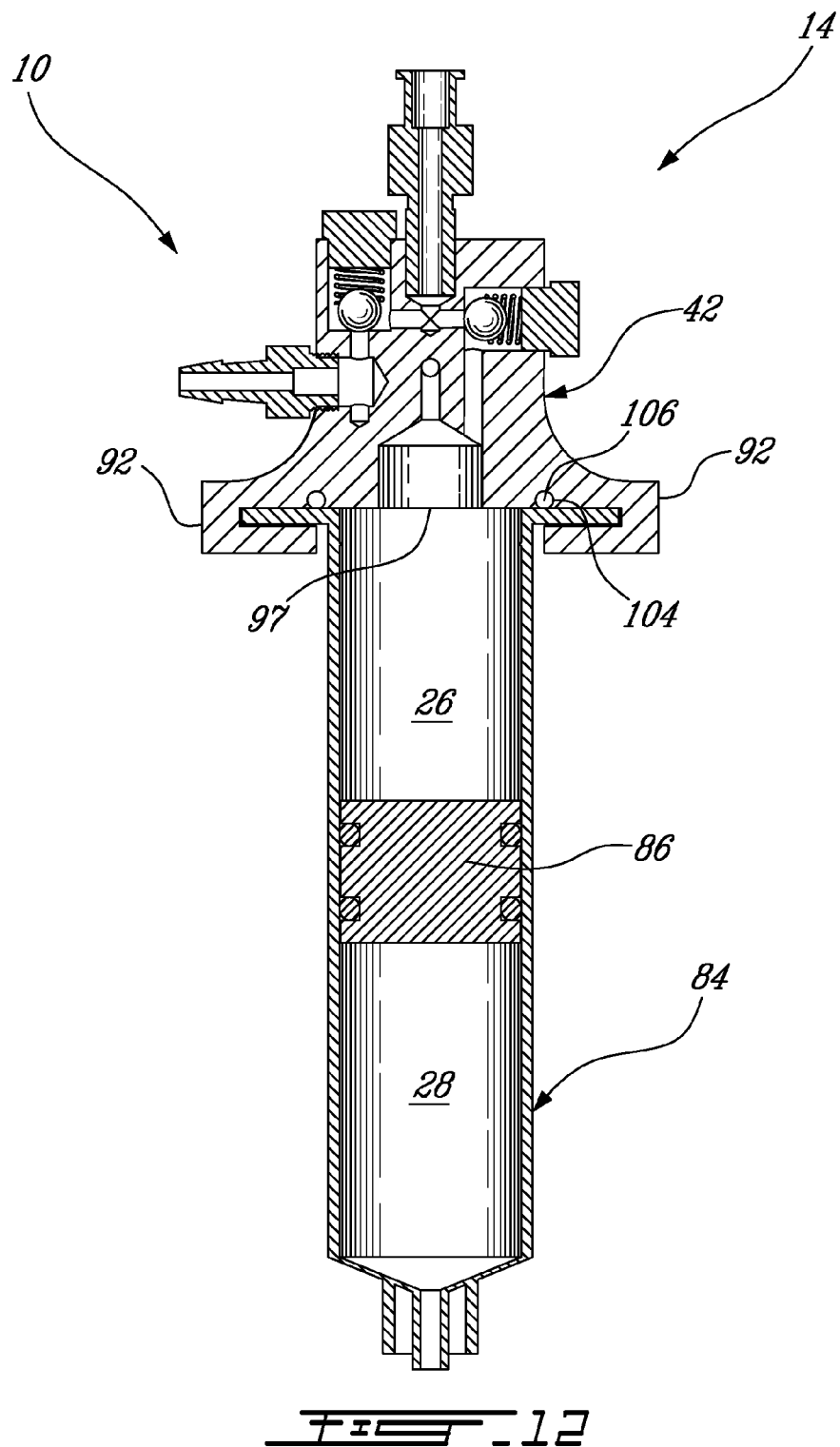
FIG. 12 is a cross-sectional view of the device in accordance with a seventh embodiment of the present invention.

FIG. 12 illustrates a seventh embodiment of the device 10, which is very similar to the sixth embodiment above-described. Similar reference numerals have been employed to identify like features. The seventh embodiment differs from the sixth embodiment only in that the housing 42 of the pressure applicator 14 does not include a cylindrical portion. Rather a circumferential notch 104 is defined in the bottom surface 52 of the housing 42 and an o-ring 106 is seated within. In this embodiment, the orientation of the o-ring 106 and notch 104 is such that the seal in formed with the top of the flange 94 of the syringe container 84, preferably adjacent the proximal inlet thereof.

Figure 13:
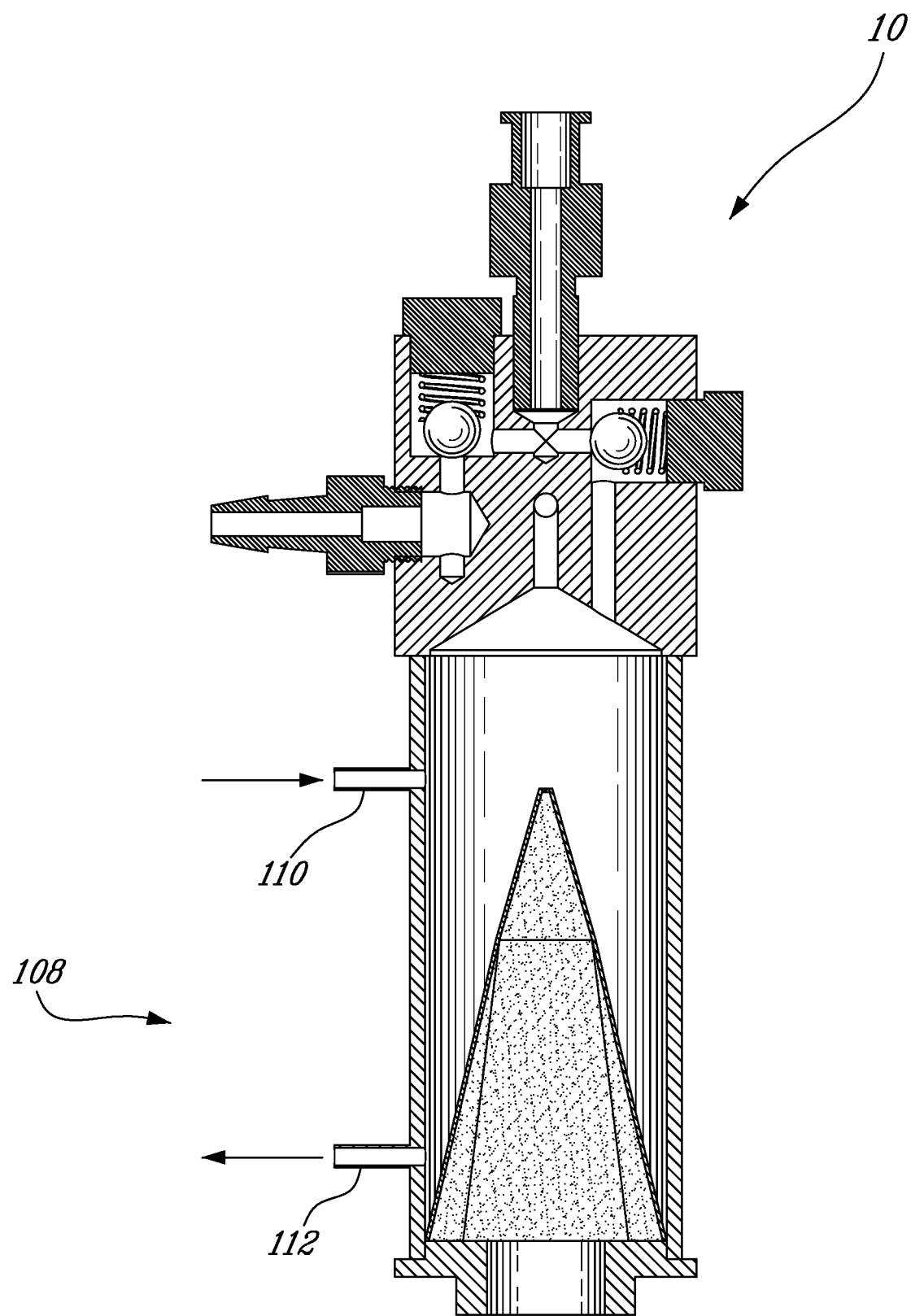
FIG. 13 is a cross-sectional view of the device in accordance with a eighth embodiment of the present invention, showing a temperature control system.

FIG. 13 illustrates an eighth embodiment of the device 10, which comprises a temperature control system 108. In this embodiment the container 12 includes inlet and outlet ports 110, 112 as part of the temperature control system 108 for heating or cooling the incompressible fluid. For example, a closed loop fluid circulation system can be used to circulate heated or cooled incompressible fluid in the container without affecting the pressure therein. A radiator or cooling jacket (not shown) can be part of the temperature control system 108 for heating or cooling the circulating fluid. The material-moving member 24 is capable of heat transfer such that the temperature of the viscous material in the container 12 can be controlled. In another example, the container 12 may be provided with a cooling or heating jacket built in the walls thereof. Generally, the temperature control system 108 allows a surgeon to achieve a better control of the viscous material. For example, cooling the viscous bone cement allows for a better control of the exothermic autocatalytic reaction so that a longer safer working viscosity can be achieved. In another example, other materials may require heat input to initiate reaction, to control working viscosity, to control polymerization temperature or to control melting transitions of injected gelling materials.

Generally, the device 10 is advantageous in that it provides sufficient mechanical advantage to the operator so that high viscosity materials may be injected while remaining small, compact and simple in design so that it can be mounted in closest proximity onto a bone biopsy cannula allowing for the injection of multiple devices concurrently (e.g., during multilevel bone cement augmentation procedures in the spine). Due to the consequently minimized distance between the viscous material container 12 and the intended injection site, actual pressure requirements, compared to prior art solutions, are always lower. This inherently lower pressure potentially reduces system compliance and, because of the generally lower pressures, does not require the device to be as bulky as some competitor devices. Also, the device can supply sufficient viscous material to complete an application without needing to be refilled. It should be noted that the cannula can be any standard cannula or the device disclosed in PCT Application PCT/CA05/000222, which is herewith incorporated by reference.

FIG. 14 illustrates an exploded view of a ninth embodiment of the device 10 for use with the viscous material injection medium 116 disclosed in PCT Application PCT/CA05/000222. In this embodiment the container 12 is provided with an elongated tip 114 attached to the distal end 20 in fluid communication with the outlet 22. The elongated tip 114 advantageously diminishes the distance that the viscous material needs to travel through a narrow cannula to get to the injection site. By filling up the elongated tip 114 with viscous material and inserting same into the injection medium 116 below the skin level identified by 118 of the patient, the surgeon can avoid the additional distance it would take for the viscous material, upon priming the system, to travel from the container 12 through an ordinary injection cannula into the receiving body. Also, dead space in the cannula, which otherwise is filled with air and is pushed by the cement into the receiving body, is greatly reduced, thus minimizing the risk of an air emboli or adverse filling patterns caused by entrapped air.

The device 10 may be sold as a kit that includes the pressure applicator 14 and the container 12, either integral or not, the detachable flexible bag and a cannula of any type.

The above description is meant to be exemplary only, and one skilled in the art will recognize that changes may be made to the embodiments described without departure from the scope of the invention disclosed. Still other modifications that fall within the scope of the present invention will be apparent to those skilled in the art, in light of a review of this disclosure, and such modifications are intended to fall within the appended claims.

The invention claimed is:

1. A device for injecting a high viscosity material into a cannula, comprising:
   a container being non-compliant and having an outlet adapted to communicate with the cannula for transferring the high viscosity material thereto;
   a pressure applicator in fluid communication with the container, the pressure applicator defining a fluid flow path through which an incompressible fluid is displaceable, the pressure applicator having:
   a housing having a fluid inlet, a fluid outlet and the fluid flow path defined therebetween, the fluid outlet disposed along the fluid flow path downstream of the fluid inlet and in fluid flow communication with an incompressible fluid receiving portion within the container;
   the housing of the pressure applicator enclosing at least a first and a second check valve disposed within the housing and in the flow path controlling the fluid flow, the first check valve being downstream of the fluid inlet and the second check valve being upstream of the fluid outlet, each of the first and second check valves permitting only one-way fluid flow therethrough; and a power piston connected to the housing in fluid flow communication with the flow path and having a piston outlet disposed within the housing between the first and second check valves and between the fluid inlet and the fluid outlet, the power piston being repeatedly manually displaceable between an extended position and a depressed position thereof to generate a build-up of pressure within the housing, wherein the power piston generates a negative pressure within the housing to draw the incompressible fluid in through the fluid inlet and the first check valve when displaced from the depressed to the extended position, and the power piston generates a positive pressure within the housing to force the incompressible fluid along the fluid flow path and out through the second check valve and the downstream fluid outlet to the container when displaced from the extended position to the depressed position, the first and second check valves and the power piston acting together to form a manually operated pump; and a pressure relief valve within the housing of the pressure applicator for equalizing pressure in the device, the pressure relief valve being in fluid communication with the incompressible fluid receiving portion for equalizing the pressure therein with atmospheric pressure when the pressure relief valve is activated; and a material-moving member attached to the container and disposed therewithin, the material-moving member including a membrane that is elastically extendable by the pressure of the incompressible fluid acting thereagainst, the membrane interrupting the fluid flow path and defining the incompressible fluid receiving portion on one side thereof and a high viscosity material receiving portion on an opposed side, the incompressible fluid receiving portion being in communication with the fluid flow path of the pressure applicator and the high viscosity material receiving portion being in communication with the outlet of the container, the membrane being displaceable by the pressure of the incompressible fluid acting thereagainst to force the high viscosity material out of the high viscosity material receiving portion of the container and into the cannula.

2. The device defined in claim 1, wherein the incompressible fluid receiving portion defines a first volume and the high viscosity material receiving portion defines a second volume, and wherein movement of the material-moving member varies the first and second volumes inversely proportionally.

3. The device as defined in claim 1, wherein the pressure applicator has a housing and the material-moving member is attached in the housing.

4. The device defined in claim 1, wherein the membrane includes a double membrane defining a first and a second membrane.

5. The device defined in claim 4, wherein the first membrane is attached to the pressure applicator and the second membrane is attached to the container, and wherein the incompressible fluid receiving portion is included entirely within the pressure applicator and the high viscosity material receiving portion is included entirely within the container, the pressure applicator being detachable from the container without exposing the incompressible fluid and viscous material contained respectively therein.

6. The device defined in claim 1, wherein the container has an elongated tip at a distal end thereof adapted for insertion in the cannula, the outlet of the container being thereby proximate to a tip of the cannula.

7. The device defined in claim 1, wherein the container and the pressure applicator are integrally joined together.

8. The device defined in claim 1, wherein the container and the pressure applicator are remote from each other and connected by a non-compliant extension line providing fluid flow communication therebetween.

9. The device defined in claim 1, wherein the pressure relief valve is fail safe and includes a biased pin portion movable between a depressed position and a released position, when in the depressed position the relief valve allowing the pressure build up and when in the released position the relief valve releasing the pressure build up from the incompressible fluid receiving portion.

10. The device defined in claim 1, wherein the incompressible fluid receiving portion enables the creation of negative pressure therein.

11. The device defined in claim 1, further comprising a pressure gauge disposed in the flow path through the pressure applicator, the pressure gage being located downstream of the second check valve.

12. The device defined in claim 1, further comprising a temperature control system for adjusting the temperature of the high viscosity material.

* * * * *